United States Patent [19]

Hjertén et al.

[11] Patent Number: 4,645,757
[45] Date of Patent: Feb. 24, 1987

[54] AGENT FOR PREVENTING OR TREATING INFECTIONS IN HUMAN BEINGS AND ANIMALS

[75] Inventors: Wilhelm E. S. Hjertén, Uppsala; Torkel M. Wadström, Knivsta, both of Sweden

[73] Assignee: Landstingens Inkopscentral Lic Ekonomisk Forening, Solna, Sweden

[21] Appl. No.: 575,160

[22] Filed: Jan. 30, 1984

Related U.S. Application Data

[63] Continuation of Ser. No. 402,349, Jul. 27, 1982, abandoned.

[30] Foreign Application Priority Data

Jun. 21, 1979 [SE] Sweden ................................ 7905523

[51] Int. Cl.$^4$ .................. A61K 31/715; A61K 31/72; A61K 31/725
[52] U.S. Cl. ........................................ 514/54; 424/92
[58] Field of Search ................. 424/92, 180, 361, 362

[56] References Cited

U.S. PATENT DOCUMENTS

| | | | |
|---|---|---|---|
| 3,130,126 | 4/1964 | Novak | 424/180 |
| 3,224,941 | 12/1965 | Nash et al. | 424/78 |
| 3,545,442 | 12/1970 | Wicker et al. | 424/78 |
| 3,624,209 | 11/1971 | Granatek et al. | 424/79 |
| 3,725,541 | 4/1973 | Queuille et al. | 424/80 |
| 3,733,400 | 5/1973 | Queuille et al. | 424/81 |
| 3,745,214 | 7/1973 | Queuille et al. | 424/78 |
| 3,903,268 | 9/1975 | Balassa | 424/28 |
| 3,911,116 | 10/1975 | Balassa | 424/28 |
| 3,914,413 | 10/1975 | Balassa | 424/28 |
| 3,943,247 | 3/1976 | Kamatsu | 424/180 |
| 3,960,720 | 6/1976 | Porath et al. | 260/112.5 R |
| 3,965,263 | 6/1976 | Swimm | 424/184 |
| 4,002,173 | 1/1977 | Manning et al. | 424/28 |
| 4,041,152 | 8/1977 | Chany | 424/85 |
| 4,046,722 | 9/1977 | Rowland | 424/85 |
| 4,137,401 | 1/1979 | Lemieux et al. | 424/85 |
| 4,225,580 | 9/1980 | Rothman et al. | 424/78 |
| 4,241,054 | 12/1980 | Volpenheim et al. | 424/180 |
| 4,260,602 | 4/1981 | Moreno | 424/180 |

FOREIGN PATENT DOCUMENTS

| | | |
|---|---|---|
| 386067 | 2/1933 | United Kingdom . |
| 904874 | 9/1962 | United Kingdom . |
| 1090421 | 11/1967 | United Kingdom . |
| 1180960 | 11/1970 | United Kingdom . |
| 1544434 | 4/1979 | United Kingdom . |

OTHER PUBLICATIONS

Smythe, C. et al., Infection and Immunity, vol. 22, pp. 462-472, 1976.
Martin, G. J., "Ion Exchange and Adsorption Agents in Medicine", Boston, Toronto, pp. 33-35 and 54-57, 195.
J. Chromatograpy, vol. 101, pp. 281-288, 1974.

Primary Examiner—Blondel Hazel
Attorney, Agent, or Firm—Fred Philpitt

[57] ABSTRACT

An agent for preventing or treating infections in human beings and animals and consisting of or containing (a) a physiologically acceptable polymer based on one or more polymeric or polymerized carbohydrates or sugar alcohols or derivatives thereof and containing hydrophobic groups and having a molecular weight which is sufficiently high to prevent it from readily penetrating cellular membrane or (b) a physiologically acceptable water-insoluble inorganic material, which exhibits a hydrophobic organic or inorganic surface layer.

15 Claims, No Drawings

AGENT FOR PREVENTING OR TREATING INFECTIONS IN HUMAN BEINGS AND ANIMALS

This is a continuation of application Ser. No. 402,349, filed July 27, 1982, now abandoned.

The present invention relates to an agent for preventing or treating infections in human beings and animals.

For the purpose of curing intestinal sicknesses caused by toxins produced by microorganisms it has been proposed that the patient is treated with ion-exchangers, such as cholestyramine (J. Am. Med. Ass. 1975, 231: 1157). In this method the toxins are bound to the ion-exchangers. A disadvantage herewith, however, is that other substances present in the intestines, such as gall salts, vitamins, digestive enzymes and certain hormones and the like are also bound to the ion-exchanging substances, causing digestive disorders, metabolic imbalances, etc.

The present invention is based on the fact that pathogenic bacteria strains are often adsorbed on substances or substance parts having a hydrophobic structure, to a much greater extent that are non-pathogenic strains. Consequently, it is suggested in accordance with the invention that there is used a physiologically acceptable substance having a sufficient degree of hydrophobicity at physiological salt concentrations to prevent adhesion of the pathogenic strains to a cell tissue, e.g. a mucous membrane, or to break such adhesion if already established, and in this way interrupt any infectious condition which may have commenced.

In accordance herewith there is provided an agent comprising or containing (a) a physiologically acceptable polymer based on one or more polymeric or polymerized carbohydrates or sugar alcohols or derivatives thereof and containing hydrophobic groups and having a molecular weight which is sufficiently high to prevent the polymer from readily penetrating the cellular membrane, or (b) a physiologically acceptable, water-insoluble inorganic material which exhibits a hydrophobic organic or inorganic surface layer.

By "infection" is meant here a state of illness caused by microorganisms (such as bacteria, virus, parasites) either directly or indirectly, e.g. by toxin formation.

The aforementioned physiologically acceptable polymer containing hydrophobic groups may be insoluble or soluble in water; in the first mentioned case, however, it is an advantage if the polymer is swellable in water, while in the last mentioned case the polymer shall have a molecular weight sufficiently high to prevent it from readily penetrating the cellular membrane.

The polymer is based on one or more polymeric or polymerized carbohydrates or sugar alcohols or derivatives thereof. Examples hereof include polysaccharides, such as dextran, agarose, cellulose, starch, xantan or derivatives thereof. Soluble products can be based, for example, on dextran or starch, while the insoluble products can be based, for example on cellulose. In the case of insoluble products, a particular advantage is afforded when the polymer has the form of a water-insoluble and water-swellable three-dimensional network held together by covalent bonds. This three-dimensional network can be obtained, to advantage, by cross-linking said polymers exhibiting hydroxyl groups from the group polymeric or polymerized carbohydrates or sugar alcohols, preferably polysaccharides, e.g. glucans, such as dextran, starch, cellulose, pullulan and pustulan, galactans, such as agarose, mannans, arabinans, xylans, alginates, etc., or derivatives thereof, by means of bridges having bonds of a covalent nature, said network exhibiting hydrophilic groups, such as hydroxyl groups.

The cross-linking of such practically endless three-dimensional networks can be effected by reacting hydroxyl-group containing polymeric or polymerized carbohydrates or sugar alcohols, preferably polysaccharides, or derivatives thereof with an at least bifunctional cross-linking agent.

For the purpose of obtaining cross-linking bridges bound to the polymer chains, e.g. to the polysaccharide chains, over ether bonds, the hydroxyl-group containing polymer, e.g. the polysaccharide or polysaccharide derivative can be reacted, e.g. in an alkaline aqueous solution, with a cross-linking agent of, for example, the type

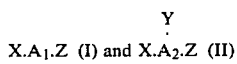

in which X, Y and Z are each a halogen atom, preferably chlorine or bromine, and $A_1$ and $A_2$ are each a straight or branched aliphatic, saturated hydrocarbon chain which is substituted with one or more hydroxyl groups and which preferably contains 3–20 carbon atoms, e.g. 3–10 carbon atoms and which is optionally broken by one or more oxygen atoms, or corresponding epoxide compounds obtainable from the compound (I) or (II) by splitting-off hydrogen halide. Examples of bifunctional substances having the formula $X.A_1.Z$ and corresponding epoxide compounds obtainable from $X.A_1.Z$ by splitting-off hydrogen halide include:

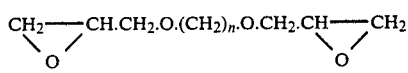

where n is an integer, e.g. from 2 to 4, and

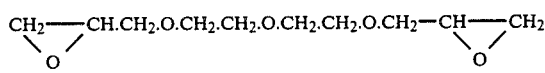

and

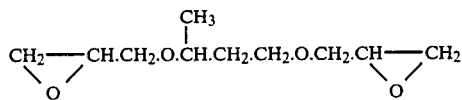

and

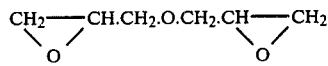

and

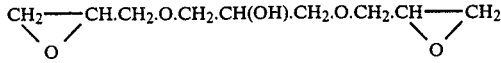

or corresponding halogen hydrins, and bifunctional glycerol derivatives of the formula $X.CH_2.CH(OH).CH_2.Z$, e.g. dichlorohydrin and dibromohydrin or corresponding epoxy compounds obtainable by splitting-off hydrogen halides and having the formula

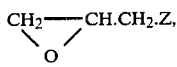

e.g. epichlorohydrin and epibromohydrin.

A further example of such a bifunctional compound is 1,2-3,4-diepoxybutane having the formula

Examples of tri-functional cross-linking agents comprising epoxy compounds corresponding to compounds of the formula $$X.A_2.Z,\text{ include}$$
$$\overset{Y}{\cdot}$$

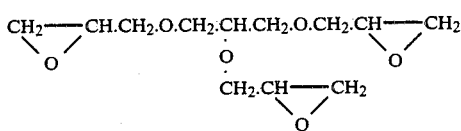

The hydroxyl-group containing polymer, e.g. the polysaccharide or polysaccharide derivative, is reacted with an at least bifunctional cross-linking agent in an amount such that there is formed a gel which is insoluble in water, i.e. a practically endless three-dimensional network having the desired properties. One skilled in this art can readily establish empirically suitable mutual quantities of different hydroxyl-group containing polymers, e.g. polysaccharides and polysaccharide derivatives and cross-linking agent.

Other cross-linking agents than those mentioned can also be used.

The cross-linking reaction also often results (in addition to the formation of bridges) in the introduction of single-bound substituents (e.g. monoethers) from the cross-linking agent, i.e. only one reactive group in the at least bifunctional cross-linking agent has reacted with a hydroxyl group in a polymeric chain, e.g. a polysaccharide chain, while the other reactive group or groups in the cross-linking agent has or have, for example, instead reacted with, e.g. water, to form e.g. hydroxyl groups etc. Consequently the polymeric product often also exhibits single-bound substituents originating from the cross-linking agent; e.g. —O.CH$_2$.CH(OH).CH$_2$OH when the cross-linking agent is epichlorohydrin, and —O.CH$_2$.CH(OH).CH$_2$.O.(CH$_2$)$_4$.O.CH$_2$.CH(OH).CH$_2$OH when the cross-linking agent is 1,4-butanediol diglycideether.

The cross-linking of hydroxyl-group containing carbohydrates (e.g. polysaccharides and oligosaccharides) and sugar alcohols and derivatives thereof is well-known to the art. (See for example British patent specification Nos. 854 715, 974 054 and 1 013 585, and the U.S. patent specification No. 3 300 474.)

The polymeric substance may also comprise a combination of two or more polymeric materials.

Hydrophobic groups are bound to the insoluble or soluble basic polymer skeleton, preferably by bonds of a covalent nature. The number of hydrophobic groups and their nature is adapted so to obtain the desired hydrophobicity, and accordingly the desired effect on the microorganisms, attention also being paid to the number and nature of hydrophilic groups which may be present. Thus, it is possible to achieve with, for example, agents containing a large number of lower alkyl groups as the hydrophobic substituent effects or results which are comparable with those obtained with agents exhibiting a smaller number of higher alkyl groups as the hydrophobic substituent. A suitable degree of substitution for each substituent or combination of substituents can be readily established in each single case by simple experiments, including the examination of the extent to which the microorganisms are bound at physiological salt concentrations (e.g. in the presence of 0.9% sodium chloride solution in water), to agents of varying degrees of substitution.

The hydrophobic groups are placed in branches projecting from the polymeric basic skeleton. The hydrophobic groups may be bound directly to the basic polymeric skeleton with carbon-carbon-bonds, although said groups are preferably bound to said network over a bridge-forming link, e.g. an ether bridge, an ester bridge or an amide bridge, or, to advantage, over a longer bridge-forming link in which case said groups are spaced from the polymeric basic skeleton.

The hydrophobic groups selected may, to advantage, be hydrocarbon chains which may be straight, branched or ring-closed, saturated or unsaturated and which preferably contain at least 3 carbon atoms, e.g. at least 6 carbon atoms. The number of carbon atoms may be high. For practical reasons, however, the number of carbon atoms is at most 30, e.g. at most 20. The hydrocarbon chains may optionally also exhibit hydrophobic substituents such as halogen atoms, preferably chlorine or bromine, or alkoxy groups having preferably at most 4 carbon atoms, but may also exhibit substituents in the form of one or more hydroxyl groups or other hydrophilic groups, whereat the location and number of said groups, however, is selected so as not to lose the substantially hydrophobic character of the substituted hydrocarbon group. The hydrocarbon chains may optionally be broken by one or more oxygen or sulphur atoms. Preferably there are selected hydrophobic groups containing at least 4, e.g. at least 6, such as at least 8 carbon atoms joined by single or double bonds, said carbon atoms carrying only hydrogen atoms.

Examples of hydrophobic groups in the polymeric material are in accordance with the aforementioned groups of the general formula —(CH$_2$)$_n$.CH$_3$, in which n is an integer. Preferably n is at least 2, e.g. at least 5. Although n may be a large number, it is generally at most 29, e.g. at most 19. The alkyl group can, for example, be to advantage octyl or dodecyl. Further examples of hydrophobic groups in the concept of the invention are branched alkyl groups, cycloalkyl groups, such as cyclohexyl, cycloalkylalkyl groups, phenyl, phenylalkyl groups, whereat the rings in the cyclic groups may be substituted with one or more hydrophobic atoms or groups, e.g. a halogen atom, such as chloride, or an alkylene group or an alkyl group, such as methyl or ethyl, or an alkoxy group.

Examples of bridge-forming links between the hydrophobic group and the polymeric basic network include:

—O.CH$_2$.CH(OH).CH$_2$.O— or

—O.CH$_2$.CH(OH).CH(OH).CH$_2$.O—

—O.CH$_2$.CH(OH).CH$_2$.O.CH$_2$.CH(OH)$_2$.O—

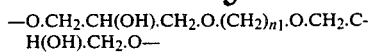

where $n_1$ is an integer of e.g. 2 to 4, or some other link having, e.g., at least two or three or more carbon atoms and being of such length that the hydrophobic group is located at a distance from the polymeric basic skeleton such that microorganisms can readily bind to the hydrophobic group.

Coupling of a hydrophobic group R to a polymer of the afore described kind, e.g. a polysaccharide or cross-linked polysaccharide, can be effected by means of substituting reactions conventional in respect of such polymers. Thus, coupling of the hydrophobic group R to the polymeric basic network through, e.g. an ether bridge, an ester bridge or an amide bridge, can be effected by means of conventional etherification techniques, esterification techniques and amide-forming reactions. Thus, reactive derivatives of R can be, for example, reacted with hydroxyl groups in the polymer. One advantageous method is to react a compound $R.X_1$, where $X_1$ is an epoxy-containing substituent, e.g.

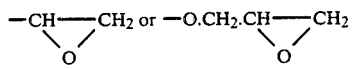

or corresponding halogen hydrin, with, e.g., hydroxyl groups in the polymer.

It is also possible, for example, to react a hydroxyl-group containing polymer and a compound ROH with a bifunctional bridge former of the kind discussed above in conjunction with the cross-linking of the polymer molecules. When introducing the substituent R, a longer bridge-forming link can also be introduced between said substituent and the polymer chains.

For the purpose of obtaining an ester-bound, or amide-bound substituent, a polymer containing hydroxyl groups or amino groups can be reacted with, for example, a compound $R.CO—X_2$, where $X_2$ is chlorine or bromine, or corresponding acid anhydrides. In this respect, $R.CO—$ may, for example be palmitoyl or stearoyl.

Dependent upon the choice of the hydrophobic groups and the field of use, the substitution degree may for instance be 0.01 to 3, such as 0.03 to 2, for instance 0.05 to 1, hydrophobic groups per monosaccharide unit or monosugar alcohol unit of the polymeric substance.

A large number of polymers of the aforementioned kinds containing hydrophobic groups are previously known from, for example, the British patent specification No. 1 527 502 as a carrier material in immunochemical assay methods carried out in vitro. A number of these polymers are also commercially available. Thus, available on the market are products based on cross-linked (with glycerol ether bridges) agarose, with octyl and phenyl groups as hydrophobic substituents (Octyl-Sepharose®CL-4B and Phenyl-Sepharose®CL-4B respectively from Pharmacia Fine Chemicals AB, Uppsala, Sweden). In this case, the octyl and phenyl group respectively are bound to the agarose network over a glycerol ether bridge.

There is preferably selected a polymer which exhibits both hydrophobic and hydrophilic groups, whereat the hydrophilic groups, for example, are hydroxyl groups. Carboxyl groups and amino groups may also be present as hydrophilic groups. When water-soluble polymers are desired, it will be understood that said polymers must also contain hydrophilic groups and the degree of substitution of the hydrophobic groups must not exceed a magnitude which will permit the product to be soluble in water to the extent required for the intended purpose. Consequently, there is normally selected a lower degree of substitution of hydrophobic groups for the soluble products than for the insoluble products. In accordance with an advantageous embodiment, the insoluble polymers contain hydrophilic groups and are swellable in water, and are thereby more readily accessible to the microorganisms and also more acceptable for, e.g., oral administration, and also more readily suspendable in aqueous liquids.

The molecular weight of the polymeric substance can be selected within wide limits, depending upon the field of use, and may be practically endlessly high when an insoluble polymer comprising a cross-linked, practically endless three-dimensional polymeric network is chosen. No requirement need normally be placed on the molecular weight when a completely insoluble polymeric substance is used. Normally, (in order to prevent the polymeric substance from readily penetrating the cellular membrane), there is chosen for the polymeric substance, particularly when it is soluble, a mean molecular weight above 800, preferably above 1000, for example above 5000. When insoluble polymers which are not cross-linked are used there is normally chosen a molecular weight lower than 50 000 000, preferably lower than 10 000 000, and often lower than 1 000 000. Such high molecular weights may be applicable for, for example, external administration and oral administration. When a soluble polymer is to be used for parental administration, there is normally selected a polymer whose molecular weight is lower than 200 000, preferably lower than 100 000, e.g. lower than 40 000. When excretion of a soluble polymer with the urine without preceding degradation is desired after parental administration, there is normally chosen a molecular weight which is lower than 30 000 but higher than 800, e.g. lower than 20 000 but higher than 1000 or 5000. When a polymer, e.g. a soluble polymer, is intended for external use or for body cavities with external orifices, the molecular weight may be within the widest of the aforementioned limits.

According to one embodiment, the polymer may contain ion-exchange groups, such as carboxyl groups and/or amino groups. This embodiment is chosen when the same polymeric material is required to bind not only to the pathogenic bacteria but also toxins or other metabolites originating therefrom. Examples of water-soluble polymers for use in agents according to the invention include physiologically acceptable polysaccharides (dextran or starch) substituted with groups of the formula $—O—CH_2—CH(OH)—R$, $—O—CH_2—CH(OH)—CH_2—O—R$, or $—O—CO—R$, e.g. $—O—CO—(CH_2)_2.CH_3$ and $—O—CO—(CH_2)_6—CH_3$, which, for example, have been found able to bind themselves to virus, e.g. influenza virus, at physiological salt concentrations and to inhibit their growth.

Examples of water-insoluble polymers for use in agents according to the invention include agarose and agar or cross-linked agarose, agar or dextran (e.g. cross-linked with hydroxyl-group containing bridges, e.g. obtained with the aid of epichlorohydrin or 1,4-butanediol diglycidether) substituted with groups of the formula $—O—CH_2—CH(OH)—R$, $—O—CH_2—CH(OH)—CH_2—O—R$ or $—O—CO—R$, e.g. $—O—CO—(CH_2)_{14}.CH_3$ or $—O—CO—(CH_2)_{16}.CH_3$, which have been found able to bind pathogenic *E. coli* at physiological salt conditions and to inhibit their growth.

Agents which can also be used in accordance with the invention include a physiologically acceptable water-insoluble inorganic material which exhibits a hydrophobic organic or inorganic surface layer. Examples of such substances include particles of silica (silicon dioxide), silica gel (i.e. silicic acid dehydrated to different degrees) and water-insoluble silicates which have been provided with a surface layer of a hydrophobic organic or inorganic material. This layer can, for example, be obtained by previously known silylating reactions. For example, $$-\underset{|}{\overset{|}{Si}}-OH$$

groups in the surface layer of said silicon compounds can be reacted with $$(CH_3-O)_3-Si(CH_2)_3-O-CH_2-\underset{O}{\underset{\diagdown\;\diagup}{CH-CH_2}}$$

whereat the substituent $$-(CH_2)_3.O.CH_2.\underset{O}{\underset{\diagdown\;\diagup}{CH-CH_2}}$$

is introduced, which substituent can be used for introducing the hydrophobic group, —R according to the above. For example, the introduced epoxide group can be reacted with an amine or alcohol containing the hydrophobic group R, e.g. with an amine $NH_2$—R. It is also possible to react directly with a compound $(CH_3-O)_3.Si$—R or $Cl_3.SiR$ for introducing hydrophobic groups. For example, hydrophobic groups may also be bound to the outer layer of said silicon compounds by reacting said compounds with a compound $Cl.Si(R)_3$, e.g. $Cl.Si(CH_3)_3$, whereat trimethylsilyl groups are introduced into the surface layer. The substituents R in the compound $Cl.Si(R)_3$ can also be different hydrophobic substituents. It is also possible to treat, e.g. silica with thionylchloride, whereafter the obtained $\equiv Si$—Cl groups can, e.g. be reacted with $NH_2.R$ or HO.R for introducing hydrophobic groups.

Other methods of binding to said silicon compounds organic groups which contain a hydrophobic group R or which can be substituted with a hydrophobic group R are also known, and can, in principle, be used for preparing the hydrophobic particles for use in agents according to the invention.

The same hydrophobic groups R can be used as those in the aforementioned organic polymers.

However, when using particles of said inorganic substances, hydrophobic R-groups having fewer carbon atoms can be used than when the aforementioned organic polymers are selected. Thus, in this case the group R may contain, for example, 1–30 carbon atoms, e.g. 1–20 carbon atoms. For example, the group R is present in trimethylsilyl groups in the outer layer of the particles, whereat $(CH_3)_3.Si$ groups thus function as hydrophobic groups. In the aforementioned groups, R, one or more carbon atoms in a hydrocarbon residue can be exchanged for silicon atoms.

Silica particles having trimethylsilyl groups in the outer layer are commercially available, and have been found suitable for use in agents according to the invention, and have been found, for example, able to bind virus at physiological salt concentrations and to inhibit their growth.

In a similar manner, particles of titanium and aluminium oxides or hydroxyapatite can be used as a water-insoluble, inorganic basic material. In addition to exhibiting hydrophobic groups in their outer layer, the particles may also exhibit hydrophilic groups, e.g. hydroxyl groups, and can thus be made more readily suspendable in aqueous liquids. Such hydrophilic groups may be present in the surface layer of the original particles or may be introduced into said surface layer in a manner similar to the hydrophobic groups. For example a part of the afore mentioned, inserted epoxide groups may be converted to —CH(OH).CH$_2$OH groups or coupled to a hydrophilic substance.

As with the organic polymers, a suitable quantity of hydrophobic groups in the surface layer of the inorganic particles can be established in each individual case for each group or each combination of groups by simple experiments, including the examination of the extent to which the microorganisms are bound at physiological salt concentrations (e.g. in the presence of 0.9% sodium chloride solution in water) to agents having varying quantities of hydrophobic groups in the surface layer.

For example, experiments with influenza A virus and parainfluenza-3-virus have shown an absorption exceeding 90% at $8 \times 10^7$ virus particles and 30 mg silica particles.

The agent according to the invention may have a solid form or may be in the form of a suspension or an aqueous solution. The suspension or solution can be given a physiologically acceptable pH, ion strength and osmotic pressure in a manner that is known per se. For example, sodium chloride can be added in this respect. When the agent consists of or comprises a physiologically acceptable polymer, said agent may be in the form of shaped bodies or, preferably, in particle form. The product can be obtained in the form of shaped bodies by bulk polymerization and can be administered externally, for example for treating sores, such as burns. Water-insoluble polymers for oral administration are given a particle form, either by producing the polymer in the form of large pieces (e.g. bulk polymerization) which are then disintegrated, e.g. by grinding, or by forming said polymer directly in the form of round particles, by head polymerization (dispersion polymerization). Particles of the desired size can be recovered by fractionating processes, e.g. by screening. The particle size can, for example, lie within a range of 0.005–1000 μm, e.g. 0.1–1000 μm, such as 1–300 μm.

According to another aspect of the invention, the agent according to the invention also contains one or more other therapeutically active substances. Special advantages are obtained herewith when the further therapeutically active substance used is one which diminishes the intestinal motility, when the agent is intended for treating infections in the intestinal tract.

In order to obtain a satisfactory result the dosage of the agent according to the invention is selected in dependence on the type of infection and its localization. For example, the dosage in respect of each treatment occasion and patient may be 0.01 to 100, such as 0.05 to 20 (e.g. 0.1 to 5) gram, whereat the larger dosages may be applicable, e.g. when treating large body surfaces, and the smaller dosages, e.g. for small, local applications. The treatment process is repeated as necessary, e.g. from 1 to 4 times a day.

The agent according to the invention may be used in different forms for preventing and treating various types of infections, such as infections of the gastro-intestinal tract, genital infections, infections in oral cavities and respiratory ducts, and skin infections.

When the agent according to the invention has a form in which it is insoluble in water (preferably in the form of water insoluble particles) it can be used to advantage for preventing and treating external infections and infections in body cavities with external orifices, especially the gastro-intestinal tract. When the agent according to the invention has a form in which it is soluble in water it can also be administered parenterally, in addition to the aforementioned methods of administration, a physiologically acceptable polymer being selected which can be degraded in the body or secrete therefrom. Examples of such fields of use include infections of the urine duct, the polymer being secreted with urine either directly, or subsequent to partial degradation in the body, and exerting the desired effect in the urine ducts.

The agent according to the invention is particularly suitable for preventing and treating infections caused by pathogenic microorganisms which have in their outer layer so-called pili or other surface structures exhibiting hydrophobic interaction. Thus, one important field of use for the agent according to the invention is the prevention and treatment of diarrhoea caused by endo- and/or entero-toxin forming pathogenic *Escherichia coli* strains. Other examples include pathogenic streptococci, which, for example, cause tonsillitis, and pathogenic staphylococcii which cause skin and sore infections.

The invention will now be illustrated with reference to a number of working examples.

EXAMPLE 1

Rabbits which were six days old and taken from the same litter were treated with one dose ($10^9$ st) enterotoxin-forming *E. coli* with CFA/1 pilus antigen. In addition to this, half of the litter also received 5 ml of sedimented particle mass of agarose cross-linked with glycerol-ether bridges and substituted with palmitoyl groups (corresponding to 450 mg dry substance). The degree of substitution of the palmitoyl groups calculated per monosaccharide-unit was 0.13. All treatments were administered orally. After three days, the animals were isolated for two hours in separate cages. When examining the animals it was found that all four rabbits treated with bacteria plus gel particles having hydrophobic groups showed no signs of diarrhoea. On the other hand, three of the four rabbits treated solely with bacteria were found to have diarrhoea, which indicated an intestine infection. This experiment and similar experiments with these particles under varying conditions on rabbits show that they have a prophylactic as well as a therapeutic effect on infections caused by these *E. coli* bacteria.

Agarose cross-linked with glycerol ether bridges and substituted with palmitoyl groups was prepared in the following manner:

Agarose in bead form (4% agarose) and cross-linked with glycerol ether bridges and having a particle size of 60–140 μm in swollen condition (Sepharose ®CL-4B from Pharmacia Fine Chemicals AB, Uppsala, Sweden) was allowed to settle from water to give a gel volume of 300 ml. The gel was transferred to a glass filter and de-watered by washing with acetone and then with 1,2-dichloroethane (DCE) (about 1 liter of each). The gel was then diluted with DCE to give a total volume of 450 ml. Pyridine (4.8 ml) was then added, followed by palmitoyl chloride (17.7 ml) in DCE (90 ml) for one hour. Subsequent to stirring the mixture for two hours at 60° C., the gel was washed with DCE (about 300 ml), acetone (about 1 liter) and finally water.

The degree of substitution of the palmitoyl groups calculated per monosaccharide unit was 0.13.

EXAMPLE 2

Cells from small intestines, isolated from pieces of human intestines, were incubated with the same *E. coli*-bacteria as referred to in Example 1 in the presence of and in the absence of the same hydrophobic gel particles as those referred to in Example 1 at 20° C., in a 0.9% NaCl solution in water. Firstly there was incubated 0.1 ml of bacteria suspension (about $10^8$ bacteria) with 0.1 ml of the hydrophobic gel particles for 10 minutes, whereafter 0.1 ml of said cells in suspension (about $10^5$ cells) was added. Less than 5 bacteria adhered to each cell. In an analoguous comparison test made without the addition of the hydrophobic gel particles, 30–60 bacteria adhered to each cell.

EXAMPLE 3

100 grams of dextran ($\overline{M}_w = 110\ 000$) were dissolved in a mixture of 1 liter of formamide and 0.5 liter of pyridine. 25 ml of caprylic acid anhydride were then added and the reaction mixture was agitated over night. The reaction product was precipitated out with ethanol and re-dissolved in water and again precipitated out with ethanol, and dried. 102 grams were obtained. The substitution degree of the $CH_3-(CH_2)_6-CO-O-$ groups was 0.056 calculated per anhydroglucose unit. 20 grams of this substance and 9 grams of NaCl are dissolved in distilled water to a solution volume of one liter. The solution is sterilized by filtering and poured into sterile, 100 ml bottles, which are then sealed in a sterile fashion. The solution is suitable for external use and for treating body cavities having external orifices.

EXAMPLE 4

100 grams of dextran ($\overline{M}_w = 110\ 000$) were dissolved in 500 ml of water. 138 ml of butyric acid anhydride were added dropwise over a period of 3 hours while simultaneously maintaining the pH at 8, by adding a 5-N aqueous solution of NaOH while agitating the mixture. Subsequent to adding the butyric acid anhydride, the mixture was agitated for a further 2.5 hours. The pH was allowed to fall to 7. The product was dialyzed against water for 4 days. The solution was filtered and evaporated to one liter and precipitated out in a mixture of methanol and acetone (1:1). The precipitated product was then dried. 99 grams were obtained. The degree of substitution of $CH_3.CH_2CH_2.CO-O-$ was 0.41 calculated per anhydroglucose unit.

30 grams of this substance and 9 grams of NaCL are dissolved in distilled water to a solution volume of one liter. The solution is sterilized by filtering and poured into sterile, 20 ml bottles, which are then sealed in a sterile fashion. The solution is suitable for external use and for treating body cavities having external orifices.

EXAMPLE 5

Two sterile cultivating vessels each having 50 ml of trypticase soy broth (from Baltimore Laboratories, Cochesville, Md., USA) were prepared. To one vessel there was also added 2 grams (calculated as dry substance) of the same particles of agarose, cross-linked with glycerol ether bridges and substituted with palmitoyl groups as referred to in Example 1. Both vessels were inoculated with $10^6$ (viable count) *Staphylococcus aureus*, (strain Cowan I) bacteria, whereafter they were incubated at 37° C. for 5 hours. In the cultivation experiment without the addition of hydrophobic particles, the number of bacteria had increased to $4 \cdot 10^9$. In the cultivation experiment with the addition of the hydrophobic particles it was found that the number of bacteria had not increased, showing that the growth of the bacteria had been inhibited.

EXAMPLE 6

Two sterile cultivating vessels each having 50 ml of proteos-peptone broth (from Difco, Detroit, Mich., USA) were prepared. Also added to one of said vessels were 250 mg of particles (calculated as dry substance) of agarose cross-linked with glycerolether bridges and substituted with $CH_3-(CH_2)_7-O-CH_2-CH(OH)-CH_2-O-$ groups (Octyl-Sepharose ®CL-4B, Pharmacia Fine Chemicals, Uppsala, Sweden. The degree of substitution=0.2 moles hydrophobic substituent per mole galactose unit; particle size in water-swollen state substantially within the range of 30–170 μm). Both vessels were inoculated with $10^5$ (viable count) *Streptococcus pyogenes* (group A, type 12 NY5) bacteria, whereafter the vessels were incubated at 37° C. for 5 hours. In the cultivation experiment without the addition of hydrophobic particles, the number of bacteria had increased to $10^9$. In the cultivation experiment with the addition of the hydrophobic particles, the number of bacteria had not increased significantly, showing that these particles impeded the growth of the bacteria.

EXAMPLE 7

15 grams of sterile silica particles exhibiting trimethylsilyl groups on the surface thereof (HDK silica particles from Wacker-Chemie GmbH, Munich, Fed. Rep. of Germany, size of primary particles=5–30 millimicrons, density of surface substituents=2–3.5/100 Å$^2$) are suspended in 1 liter of sterile aqueous 0.9% (w/v) NaCl solution. The suspension is poured in a sterile fashion into 50 ml sterilized bottles which are sealed in a sterile manner. The suspension is suitable for external use and for body cavities having external orifices.

We claim:

1. A method for preventing or treating infections
   (A) that are present on the exterior of a human being or animal, and
   (B) that are caused by pathogenic microorganisms which have in their outer layer
      (a) pili, or
      (b) other surface structures exhibiting hydrophobic interaction,
   which method comprises administering to the site of the infection on the exterior of humans or animals a therapeutically effective amount of a modified agarose, said modified agarose being
      (1) water-insoluble,
      (2) cross-linked with glycerol-ether bridges, and
      (3) substituted with palmitoyl groups.

2. A method according to claim 1 wherein said exterior of humans or animals includes body cavities having external orifices.

3. A method according to claim 1 wherein said agarose is in the form of water-insoluble particles having a size within the range of 0.1–1000 μm.

4. A method for preventing or treating infections
   (A) that are present on the exterior of a human being or animal, and
   (B) that are caused by pathogenic microorganisms which have in their outer layer
      (a) pili, or
      (b) other surface structures exhibiting hydrophobic interaction,
   which method comprises administering to the site of the infection on the exterior of humans or animals a therapeutically effective amount of a physiologically acceptable polymer
      (1) that is based on agarose or derivatives thereof, and
      (2) that contains hydrophobic groups,
         (a) which are placed in branches projecting from the agarose base skeleton,
         (b) which are straight, branched or ring-closed, saturated or unsaturated hydrocarbon claims containing at least 8 carbon atoms and at most 30 carbon atoms, and
      (3) having a molecular weight which is sufficiently high to prevent it from readily penetrating cellular membranes.

5. A method according to claim 4 wherein the polymer comprises a cross-linked agarose which is substituted with said hydrophobic groups.

6. A method according to claim 4 wherein said polymer also exhibits ion-exchange groups.

7. A method according to claim 4 wherein said polymer is in the form of water-insoluble particles having a particle size within the limits 0.1–1000 μm.

8. A method according to claim 4 wherein said hydrophobic groups are palmitoyl groups.

9. A method according to claim 4 wherein said hydrophobic groups are stearoyl groups.

10. A method according to claim 4 wherein said exterior of humans or animals includes body cavities having external orifices.

11. A method for preventing or treating infections
    (A) that are present on the exterior of a human being or animal, and
    (B) that are caused by pathogenic microorganisms which have in their outer layer
       (a) pili, or
       (b) other surface structures exhibiting hydrophobic interaction,
    which method comprises administering to the site of the infection on the exterior of humans or animals a therapeutically effective amount of a physiologically acceptable polymer
       (1) that is based on one or more polysaccharides or derivatives thereof, and
       (2) that contains hydrophobic groups,
          (a) which are placed in branches projecting from the polymeric base skeleton,
          (b) which are straight, branched or ring-closed, saturated or unsaturated hydrocarbon claims containing at least 8 carbon atoms and at most 30 carbon atoms, and
       (3) having a molecular weight which is sufficiently high to prevent it from readily penetrating cellular membranes.

12. A method according to claim 11 wherein said polymer also exhibits ion-exchange groups.

13. A method according to claim 11 wherein said polymer is in the form of water-insoluble particles having a particle size within the limits 0.1–1000 μm.

14. A method according to claim 11 wherein said hydrophobic groups are palmitoyl or stearoyl groups.

15. A method according to claim 11 wherein said exterior of humans or animals include body cavities having external orifices.

* * * * *